United States Patent [19]

Kuge et al.

[11] Patent Number: 5,602,255
[45] Date of Patent: Feb. 11, 1997

[54] PROCESS FOR PRODUCING TETRAHYDROISOQUINOLINE-3-CARBOXYLIC ACID COMPOUNDS

[75] Inventors: Yukihiro Kuge, Kawachinagano; Toru Sugaya, Nara; Shinji Tomioka, Hashimoto, all of Japan

[73] Assignee: Kyowa Hakko Kogyo Co., Ltd., Tokyo, Japan

[21] Appl. No.: 416,512

[22] Filed: Apr. 4, 1995

Related U.S. Application Data

[63] Continuation of Ser. No. 211,922, Apr. 25, 1994, abandoned.

[30] Foreign Application Priority Data

Aug. 31, 1992 [JP] Japan ..................... 4-231043

[51] Int. Cl.⁶ .................................. C07D 217/26
[52] U.S. Cl. ........................................ 546/147
[58] Field of Search ............................. 546/147

[56] References Cited

U.S. PATENT DOCUMENTS 4,912,221  3/1990  O'Reilly et al. .................. 546/147

FOREIGN PATENT DOCUMENTS 57-01685  1/1982  Japan .
2193969   7/1990  Japan .

OTHER PUBLICATIONS

S. Archer, "A Revised Preparation of Clemo's . . . ", Journal of Organic Chemistry, 16, pp. 430–432 (1951).
Anil K. Saxena et al., "Compounds Acting on CNS . . . ", Indian Journal of Chemistry, vol. 13, Mar. 1975, pp. 230–237.
Kimiaki Hayashi et al., "Facile Preparation of Optically . . . ", Chemical and Pharmaceutical Bulletin, 31(1), pp. 312–314 (1983).
"Bis(Chloromethyl)Ether—Chemical and Physical Data" IARC Monographs, 4, pp. 231–238 (1974).
B. L. Van Duuren et al., "bis(Chloromethyl) Ether", Org. Syn., Coll. vol. 4, pp. 101–103 (1963).
Robert R. Sealock et al., "The Synthesis, Resolution . . . " J. Amer. Chem. Soc., 73, pp. 5386–5389 (1951).
Paul L. Ornstein et al., "Synthesis of 6–Oxodecahydroisoquinoline–3–carboxylates . . . ", J. Org. Chem 56, pp. 4388–4392 (1991).
Kazmierski et al, *J. Med. Chem.*, 1988, vol. 31, No. 11, pp. 2170–2177.

*Primary Examiner*—Zinna Northington Davis
*Attorney, Agent, or Firm*—White & Case

[57] ABSTRACT

The present invention relates to a process for producing 1,2,3,4-tetrahydroisoquinoline-3-carboxylic acid compounds or salts thereof represented by the following formula (II):

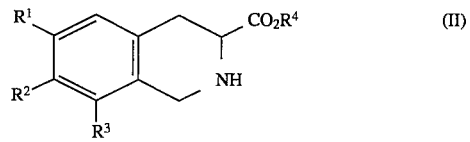

(II)

wherein $R^1$, $R^2$ and $R^3$ independently represent hydrogen, hydroxy or lower alkoxy, and $R^4$ represent hydrogen, lower alkyl, aryl or aralkyl, the process comprising, allowing phenylalanine compounds to react with formaldehyde or paraformaldehyde in the presence of sulfuric acid or hydrobromic acid, the phenylalanine compounds being represented by the following formula (I):

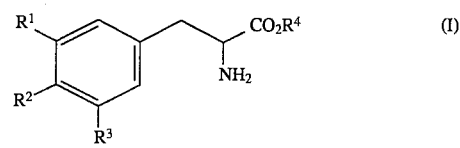

(I)

wherein $R^1$, $R^2$, $R^3$ and $R^4$ have the same meaning as defined above.

5 Claims, No Drawings

PROCESS FOR PRODUCING TETRAHYDROISOQUINOLINE-3-CARBOXYLIC ACID COMPOUNDS

This application is a 371 of /JP/93/00933 filed Jul. 7, 1993 which is a continuation of application Ser. No. 08/211,922 Apr. 25, 1994 now abandoned.

TECHNICAL FIELD

The present invention relates to a process for safely producing 1,2,3,4-tetrahydroisoquinoline-3-carboxylic acid derivatives useful as medical intermediates.

PRIOR ART

A process for producing 1,2,3,4-tetrahydroisoquinoline-3-carboxylic acid derivatives by allowing phenylalanine derivatives to react with formaldehyde or paraformaldehyde in the presence of an acid is known as the Pictet Spengler reaction [Journal of Organic Chemistry, 16, 430 (1951), Indian Journal of Chemistry, 13, 230 (1975), Chemical and Pharmaceutical Bulletin, 31(1), 312 (1983), and Japanese Published Unexamined Patent Application Nos. 16865/82 and 193969/90].

In these known methods, hydrochloric acid is used as an acid catalyst. However, in this case, it has been known that bis(chloromethyl)ether, which is a strong mutagen [IARC Monographs, 4, 231 (1974)], is formed through the reaction of hydrochloric acid with formaldehyde or paraformaldehyde [Organic Synthesis Coll. Vol. 4, 101–103 (1963)].

Further when hydrochloric acid is used as an acid catalyst, the resultant product of the Pictet Spengler reaction using L-phenylalanine as a substrate has an optical purity of 50 to 85% ee and accompanies a high degree of racemization. (Japanese Published Unexamined Patent Application No. 193969/90).

DISCLOSURE OF THE INVENTION

The present invention relates to a process for safely producing 1,2,3,4-tetrahydroisoquinoline-3-carboxylic acid derivatives [hereinafter referred to as "Compound (II)"] or salts thereof represented by the following formula (II):

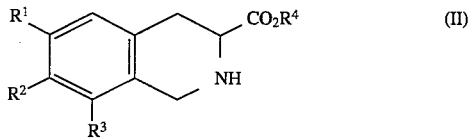

wherein $R^1$, $R^2$, and $R^3$ independently represent hydrogen, hydroxy or lower alkoxy, and $R^4$ represent hydrogen, lower alkyl, aryl or aralkyl, the process comprising, allowing phenylalanine derivatives to react with formaldehyde or paraformaldehyde in the presence of sulfuric acid or hydrobromic acid, the phenylalanine derivatives being represented by the following formula (I):

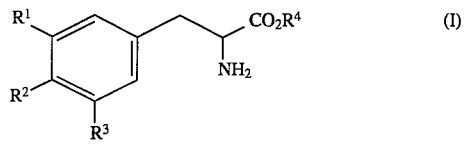

wherein $R^1$, $R^2$, $R^3$ and $R^4$ have the same meaning as defined above.

In the definition of $R^1$, $R^2$, $R^3$, the lower alkyl and the alkyl moiety in the lower. alkoxy mean a straight chain or branched alkyl group having 1 to 6 carbon atoms such as methyl, ethyl, propyl, isopropyl, butyl, isobutyl, sec-butyl, tert-butyl, pentyl, isopentyl, neopentyl and hexyl. The aryl means phenyl or naphthyl. The aralkyl means benzyl, phenethyl or trityl each having 7 to 20 carbon atoms. The salts of Compound (II) include sulfates and hydrobromides.

The process for producing Compound (II) is described below.

Compound (II) can be obtained by allowing Compound (I) to react with formaldehyde or paraformaldehyde in an aqueous sulfuric acid solution or hydrobromic acid.

The concentration of the aqueous sulfuric acid solution is in the range of 0.001 to 12N, preferably 0.01 to 1N.

The concentration of solution of hydrobromic acid is in the range of 20 to 50%.

Compound (I) is synthesized by the method disclosed in, for example, Journal of American Chemical Society, 73, 5386 (1951).

As formaldehyde, 37 to 40% formalin is generally used in an amount of 1 to 10 equivalents, preferably 1.5 to 5 equivalents, based on Compound (I). This applies to the case of paraformaldehyde.

The reaction is carried out at 40° to 100° C. The reaction time is long when the temperature is low, and the reaction time is short when the temperature is high. With the use of the optically active Compound (I), high temperature promotes racemization. Therefore, the reaction is preferably carried out at 50° to 80° C. and completed in 0.5 to 36 hours, generally in 3 to 12 hours.

Compound (II) is generally obtained in the form of its salt. When it is desired to obtain Compound (I) in its free form, the Compound (II) may be dissolved or suspended in an alkali aqueous solution and an acid is added thereto for neutralization. Compound (I) thus formed in its free form may be isolated and purified.

Compound (II) obtained by the above production method can be isolated and purified by purification methods conventionally used in organic synthetic chemistry, for example, filtration, extraction, washing, drying, concentration, recrystallization, and various kinds of chromatography.

Compound (II) obtained in the present invention can be used as a synthetic intermediate for N-methyl-D-aspartic acid receptor antagonists disclosed in, for example, Journal of Organic Chemistry, 56, 4388 (1991).

Certain embodiments of the present invention are described by referring to the following examples.

BEST MODE FOR CARRYING OUT THE INVENTION

In the following examples, optical purity was measured by high performance liquid chromatography (HPLC) under the two types of conditions:

a) Example 2

Column; SUMICHIRAL OA-5000 (L) (Sumitomo Chemistry), 4.6φ×150 mm

Mobile phase; 2 mM $CuSO_4$ solution:acetonitrile=85:15

Detection UV; 254 nm

Column temperature; 20° C.

Flow rate; 1.0 ml/min b) Example 3

Column; CROWNPAK (+) (Daicel Chemistry), 4.6φ×150 mm

Mobile phase; HClO₄ aqueous solution (pH 2.0)
Detection UV; 254 nm
Column temperature; 20° C.
Flow rate; 0.8 ml/min

EXAMPLE 1

(+)-6-Hydroxy-1,2,3,4-tetrahydroisoquinoline-3-carboxylic Acid (Compound 1)

To 61.5 g of D, L-m-tyrosine suspended in 250 ml of 0.05N sulfuric acid aqueous solution, 48 ml of 37% formalin aqueous solution was added dropwise. The reaction mixture was stirred at 70° C. for 12 hours, and subjected to crystallization under ice cooling for 2 hours. The obtained crystal were filtered off, and dried at 60° C. under reduced pressure to obtain 65.6 g of Compound 1 (yield 100%). Compound 1 thus obtained was dissolved in an aqueous solution of 2N sodium hydroxide, and was then adjusted to pH 5 with concentrated hydrochloric acid. The precipitate was filtered off, washed with water and dried at 60° C. under reduced pressure to obtain 52.5 g of purified product of Compound 1.

¹H-NMR(D₂O-NaOD) δ (ppm): 6.62 (1H, d, J=8.1 Hz), 6.23(1H, d, J=8.1 Hz), 6.19(1H, s), 3.65(1H, d, J=15.2 Hz), 3.57(1H, d, J=15.2 Hz), 3.13(1H, dd, J=11.0, 3.6 Hz), 2.68(1H, dd, J=16.2, 3.6 Hz), 2.51(1H, d, J=16.2, 11.0 Hz)

EXAMPLE 2

(−)-1,2,3,4-Tetrahydroisoquinoline-3-carboxylic Acid Hydrobromide (Compound 2)

To 10 g of L-phenylalanine suspended in 108 ml of 47% hydrobromic acid, 23 ml of 37% formalin aqueous solution was added dropwise. The reaction mixture was stirred at 65° C. for 7 hours, and subjected to crystallization under ice cooling for 3 hours. The precipitate was filtered off, and dried at 55° C. under reduced pressure to obtain 13.5 g of Compound 2 (yield 86.4%, optical purity 97% ee).

¹H-NMR(d₆-DMSO) δ (ppm): 9.76(1H, br), 7.41(4H, m), 4.60(1H, dd, J=11.3, 5.1 Hz), 4.49(2H, s), 3.46(1H, dd, J=17.0, 5.1 Hz), 3.26(1H, dd, J=17.0, 11.2 Hz)

EXAMPLE 3

(−)-6-Hydroxy-1,2,3,4-tetrahydroisoquinoline-3-carboxylic Acid (Compound 3)

In the same manner as in Example 1, 61.5 g of L-m-tyrosine having an optical purity of 100% ee was allowed to react to obtain 62.3 g of Compound 3 (yield 95%, optical purity 100% ee).

INDUSTRIAL APPLICABILITY

The present invention provides a process for safely producing 1,2,3,4-tetrahydroisoquinoline-3-carboxylic acid derivatives, which are useful as medical intermediates, in a large amount without producing a mutagenic substance.

We claim:

1. A process for producing 1,2,3,4-tetrahydroisoquinoline-3-carboxylic acid compounds or salts thereof of the formula:

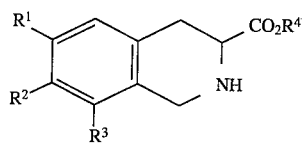

wherein $R^1$, $R^2$ and $R^3$ independently represent hydrogen, hydroxy or lower alkoxy and $R^4$ represent hydrogen, lower alkyl, aryl or aralkyl, which comprises reacting phenylalanine compounds with formaldehyde or paraformaldehyde in the presence of sulfuric acid or hydrobromic acid, the phenylalanine compounds being:

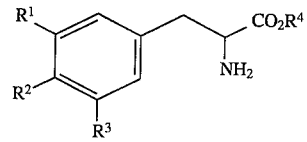

wherein $R^1$, $R^2$, $R^3$ and $R^4$ have the same meaning as defined above.

2. The process according to claim 1, in which $R^3$ is hydrogen.

3. The process according to claim 1, in which $R^3$ is hydroxy or lower alkoxy.

4. The process according to claim 2, in which each of $R^1$ and $R^2$ is hydrogen.

5. The process according to claim 2, in which $R^1$ is hydroxy and $R^2$ is hydrogen.

* * * * *

UNITED STATES PATENT AND TRADEMARK OFFICE
CERTIFICATE OF CORRECTION

PATENT NO. :   5,602,255
DATED      :   February 11, 1997
INVENTOR(S) :  Kuge et al.

It is certified that error appears in the above-indentified patent and that said Letters Patent is hereby corrected as shown below:

Col. 4, line 29, after "hydrobromic acid," delete "the" and insert --at a temperature of 50° to 80°C for a period of 3 to 12 hours, wherein said--.

Col. 4, line 30, change "being" to --are--.

Signed and Sealed this

First Day of July, 1997

Attest:

Attesting Officer

BRUCE LEHMAN
Commissioner of Patents and Trademarks